United States Patent [19]

Pissiotas et al.

[11] 4,323,388
[45] Apr. 6, 1982

[54] CYANOALKYL-PHENYLUREAS HAVING SELECTIVE HERBICIDAL ACTIVITY

[75] Inventors: Georg Pissiotas, Lörrach, Fed. Rep. of Germany; Dieter Dürr, Bottmingen; Otto Rohr, Therwil; Alfons Lukaszczyk, Basel, all of Switzerland

[73] Assignee: Ciba-Geigy Corporation, Ardsley, N.Y.

[21] Appl. No.: 240,336

[22] Filed: Mar. 3, 1981

[30] Foreign Application Priority Data

Mar. 10, 1980 [CH] Switzerland ............... 1860/80

[51] Int. Cl.$^3$ ............... A01N 47/30; A01N 47/38; C07C 127/19; C07D 295/16
[52] U.S. Cl. ............... 71/88; 71/92; 71/94; 71/95; 71/105; 260/239 BF; 260/326.4; 260/453 RW; 260/465 D; 544/58.4; 544/163; 544/390; 546/226; 548/200; 548/215; 548/341; 548/378
[58] Field of Search .... 260/465 D, 453 RW, 239 BF, 260/326.4; 71/105, 88, 92, 94, 95; 544/58.4, 163, 390; 546/226; 548/200, 215, 341, 378

[56] References Cited

U.S. PATENT DOCUMENTS

4,046,808  9/1977  Cross ............... 564/52

FOREIGN PATENT DOCUMENTS

1294009  10/1972  United Kingdom.

OTHER PUBLICATIONS

Pryne et al., J. Agric. Food Chem., vol. 27, No. 3, pp. 537–543, (1979).

*Primary Examiner*—Dolph H. Torrence
*Attorney, Agent, or Firm*—Frederick H. Rabin

[57] ABSTRACT

There have been produced novel cyanoalkyl-phenylureas which have herbicidal activity and which exhibit good selectivity in various crops of cultivated plants. The novel cyanoalkyl-phenylureas correspond to the formula I defined herein

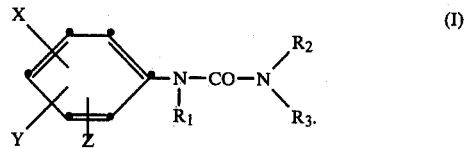

23 Claims, No Drawings

CYANOALKYL-PHENYLUREAS HAVING SELECTIVE HERBICIDAL ACTIVITY

The present invention relates to novel cyanoalkyl-phenylureas having herbicidal activity, to their production, to compositions containing them, and to their use for the selective combating of weeds in various crops of cultivated plants, for example cotton and maize, in particular however cereals and rape. Furthermore, these active substances can be used with similar success in sugar-beet crops.

Herbicidally acting phenylureas have been known and introduced for a long time. Their widespread use has resulted on the one hand in the extensive freeing of cultivated crops such as cereals from weeds, on the other hand however in a proliferation of weeds which have a greater resistance to herbicides of this type.

The novel cyanoalkyl-phenylureas according to the invention correspond to the general formula I

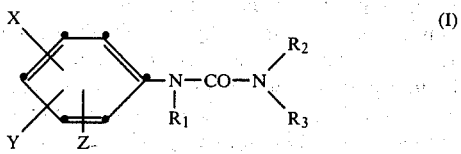

wherein
X is hydrogen, halogen, trifluromethyl, methyl or methoxy,
Y is

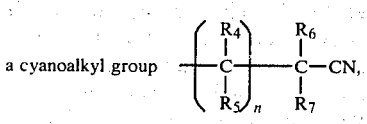

a cyanoalkyl group

Z is hydrogen or halogen,
n is the number 0, 1 or 2,
$R_1$ is hydrogen or $C_1$–$C_6$-alkyl,
$R_2$ is hydrogen, $C_1$–$C_6$-alkyl, $C_1$–$C_6$-alkoxy, $C_2$–$C_6$-alkenyl or $C_3$–$C_6$-alkynyl,
$R_3$ is hydrogen, $C_1$–$C_6$-alkyl, $C_2$–$C_6$-alkenyl, or
$R_2$ and $R_3$ together with the nitrogen atom to which they are bound form a 5–7 membered heterocycle, which can contain as ring member also an oxygen or sulfur atom or an imino group,
$R_4$, $R_5$ and $R_6$ are each hydrogen, $C_1$–$C_6$-alkyl or $C_1$–$C_6$-haloalkyl,
$R_7$ is hydrogen, $C_1$–$C_6$-alkyl, aralkyl, particularly benzyl, phenyl or $C_1$–$C_6$-alkoxy, or
$R_6$ and $R_7$ together with the carbon atom carrying them can form a $C_3$–$C_7$-cycloalkyl ring.

Halogen as a rule is fluorine, chlorine or bromine, chlorine or bromine being the preferred halogens.

By alkyl or by alkyl part of another substituent, such as alkoxy, haloalkyl or aralkyl, are meant, depending on the number of carbon atoms, the following groups: methyl, ethyl, n-propyl, i-propyl, butyl, pentyl or hexyl, as well as the corresponding isomeric groups, for example sec-butyl, i-butyl, n-pentyl or neo-pentyl.

By analogy, examples of alkoxy are accordingly: methoxy, ethoxy or i-propyloxy; of haloalkyl: chloromethyl, difluoromethyl, trifluoromethyl, 2,2,2-trifluoroethyl or perfluoroethyl; and of aralkyl: benzyl, 2-phenylethyl or 1-phenylethyl.

Alkenyl is in general: vinyl, allyl, methallyl, 1-butenyl, 2-butenyl or 3-butenyl, as well as the isomeric pentenyl and hexenyl groups, especially however allyl.

Alkynyl is for example: propargyl, 2-butynyl or 3-butynyl, as well as the isomeric pentynyl and hexynyl groups, particularly however propargyl.

According to definition, cycloalkyl groups are: cyclopropyl, cyclobutyl, cyclopentyl, cyclohexyl or cycloheptyl.

Examples of 5- to 7-membered nitrogen heterocycles are: pyrrolidine, pyrazolidine, imidazolidine, oxazolidine, thiazolidine, piperidine, piperimidine, piperazine, morpholine, thiomorpholine or perhydroazepine.

The compounds of the formula I have marked selective-herbicidal properties in general, and prove to be particularly advantageous for combating weeds in crops of productive plants such as cotton and maize, and especially in cereal crops. Individual compounds have a selective action in rape crops. It is also possible to treat sugar-beet crops with these active substances to combat weeds.

Preferred compounds of the formula I are those wherein
(a) the cyanoalkyl substituent Y occupies the para- or meta position of the phenyl ring,
(b) n is zero or one,
(c) $R_2$ is hydrogen, methyl or methoxy, and $R_3$ is methyl,
(d) $R_1$ is hydrogen,
(e) Z is hydrogen, and
(f) X is hydrogen, halogen or trifluoromethyl.

A further preference is to be given to those compounds wherein
(aa) the cyanoalkyl substituent Y occupies the para-position of the phenyl ring; and n is zero, and
(bb) the cyanoalkyl substituent Y occupies the meta-position of the phenyl ring, and n is one.

By further combination of the features of the preferred groups are obtained the following more particularly advantageous groups:
(aaa) compounds in which the substituent Y is in the para-position and the substituent X in the meta-position of the phenyl ring, n is zero, $R_1$ and Z are each hydrogen, $R_2$ is hydrogen, methyl or methoxy, $R_3$ is methyl, and X is hydrogen, chlorine or trifluoromethyl, and
(bbb) compounds in which the substituent Y is in the meta-position of the phenyl ring, n is one, $R_1$, X and Z are each hydrogen, $R_2$ is hydrogen, methyl or methoxy, and $R_3$ is methyl.

To be mentioned as preferred individual compounds are:
β-[4-(3,3-dimethylureido)-3-chlorophenyl]-propionitrile,
β-[4-(3-methoxy-3-methylureido)-3-chlorophenyl]-propionitrile,
β-[3-(3-methoxy-3-methylureido)-phenyl]-propionitrile,
β-[3-(3,3-dimethylureido)-phenyl]-propionitrile,
α-[4-(3-methoxy-3-methylureido)-3-chlorophenyl]-acetonitrile,
α-[4-(3,3-dimethylureido)-3-chlorophenyl]-acetonitrile,
α-[4-(3,3-dimethylureido)-3-trifluoromethylphenyl]-acetonitrile, and
β-[4-(3,3-dimethylureido)-3-methylphenyl]-α-methyl-propionitrile.

A total herbicidal action results however when active substances according to the invention are applied in sufficiently large amounts. The active substances can be applied both in the pre-emergence process and in the post-emergence process, and the amounts applied can vary within wide limits, for example between 0.1 and 10 kg of active substance per hectare, preferably however the amount used is between 0.5 and 5 kg of active substance per hectare.

Compositions according to the invention contain, besides an active substances of the formula I, a suitable carrier and/or other additives. Suitable carriers and additives can be solid or liquid and they correspond to the substances common in formulation practice, for example natural or regenerated mineral substances, solvents, diluting, dispersing, emulsifying and wetting agents, adhesives, thickeners, binders and/or fertilisers.

The herbicidal compositions containing an active substance of the formula I can be in the form of dusts, emulsion concentrates, granulates or dispersions, and also in the form of solutions or suspensions, all produced by customary formulation methods.

The compounds of the formula can be produced by methods known per se.

One process for producing cyanoalkyl-phenylureas of the formula I comprises reacting, in an organic solvent inert to the reactants, a correspondingly substituted aniline of the formula II

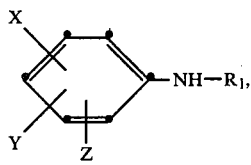   (II)

in the presence of an acid-binding agent, with a carbamoyl chloride of the formula III

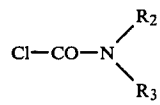   (III)

wherein X, Y, Z, $R_1$, $R_2$ and $R_3$ have the meanings defined under the formula I.

According to a further process, the cyanoalkyl-phenylureas of the formula I wherein $R_1$ is hydrogen are produced by reacting a correspondingly substituted isocyanate of the formula IV

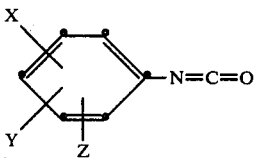   (IV)

with an amine of the formula V

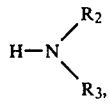   (V)

wherein X, Y, X, $R_2$ and $R_3$ have the meanings defined under the formula I.

The isocyanates IV required as starting materials are obtained by reaction of correspondingly substituted anilines of the formula VI

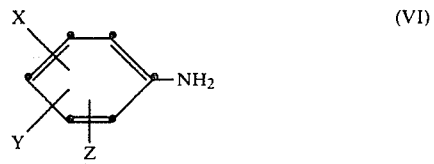   (VI)

with phosgene, where X, Y and Z have the meanings defined under the formula I.

These reactions are performed in organic solvents which are inert to the reactants, such as ketones, for example acetone, ethyl methyl ketone or cyclohexanone; esters, for example ethyl acetate; dimethylformamide; acetonitrile; ethers, such as diethyl ether, tetrahydrofuran, dioxane, and so forth. It is advantageous when the solvents are miscible with water, since the reaction product can be precipitated by the addition of water. The reaction temperatures are between 0° and 150° C., in practice between room temperature and the boiling point of the reaction mixture. The reactions are in general performed under normal pressure; larger amounts can advantageously also be produced in pressure vessels.

The compounds of the formula I are negligibly toxic to warm-blooded animals, and handling of the compounds requires no precautionary measures. They have relatively high solubility in the customary organic solvents but low solubility in water. They can be easily precipitated by the addition of water to the reaction solution. Their formulation as liquid herbicidal compositions is effected with the aid of conventional solubility-promoting agents and/or dispersing agents.

The novel active substances of the formula I are stable compounds which are soluble in the usual organic solvents, such as alcohols, ethers, ketones, dimethylformamide, dimethyl sulfoxide, and the like.

The compositions according to the invention are produced in a manner known per se by the intimate mixing and grinding of the active substances of the formula I with suitable carriers and/or distributing agents, optionally with the addition of antifoaming agents, wetting agents, dispersing agents and/or solvents, all inert to the active substances. The active substances can be obtained and used in the following forms:

solid preparations: dusts, scattering agents, granules (coated granules, impregnated granules and homogeneous granules);

water-dispersible concentrates of active substance: wettable powders, pastes, emulsions, emulsion concentrates and suspension concentrates (flowable);

liquid preparations: solutions.

The concentration of active substance in the compositions according to the invention is 1 to 80 percent by weight, and when being applied the compositions can if necessary contain the active substance also at a lower concentration, such as about 0.05 to 1 percent by weight.

Other biocidal active substances or compositions can be added to the compositions according to the invention. Thus, in order to broaden the sphere of action, the novel compositions can contain, in addition to the stated compounds of the formula I, for example insecticides, fungicides, bactericides, fungistatics, bacteriostatics, nematocides or further herbicides.

The following Examples 1 and 2 are intended to further illustrate the production of the phenylureas of the formula I according to the invention. Further compounds produced in an analogous manner are listed in the Tables 1 and 2 which follow Examples 1 and 2. The temperature values are given in degrees Centigrade, and parts and percentages relate to weight. Pressure values are in Torr (1 Torr=1.33 millibars). The processing of the active substances into commercially usable preparations and also tests to demonstrate the herbicidal activity thereof are described in subsequent Examples.

PRODUCTION EXAMPLES

Example 1

β-[3-(3,3-Dimethylureido)-phenyl]-propionitrile (Compound 101)

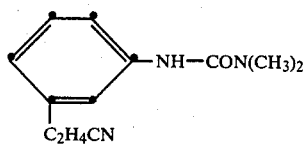

(a) 115 g of β-(3-nitrophenyl)-propionitrile are introduced into a boiling mixture of 150 g of iron turnings, 5 ml of concentrated hydrochloric acid, 100 ml of water, 300 ml of alcohol and 150 ml of toluene. The mixture is refluxed for 4 hours and is then allowed to cool. There is then added 1 liter of about 0.5 N sodium hydroxide solution, the mixture is filtered and the filter residue is washed with toluene. The toluene solutions are separated, concentrated by evaporation and the residue is distilled. The yield is 50 g of β-(3-aminophenyl)-propionitrile having a boiling point of 132°/0.08 Torr.

(b) 50 g of β-(3-aminophenyl)-propionitrile are dissolved in 100 ml of ethyl acetate, and the solution is added dropwise at −20° to a solution of 40 g of phosgene in 300 ml of toluene. This solution is stirred for 8 hours at room temperature and is subsequently refluxed for one hour. The solvent is then distilled off and the residue, consisting of oily β-(3-isocyanatophenyl)-propionitrile, which boils at 126°/0.5 Torr, is added dropwise, with stirring, to a mixture of 25 g of a 40% aqueous solution of dimethylamine in 200 ml of acetonitrile. Ice-water is finally added to the reaction solution, in consequence of which the urea precipitates. The resulting β-[3-(3,3-dimethylureido)-phenyl]-propionitrile is collected by filtration, and recrystallised from diluted ethanol; yield 33 g, m.p. 159°–161°.

Example 2

α-[4-(3-methoxy-3-methylureido)-3-chlorophenyl]-acetonitrile (Compound 23)

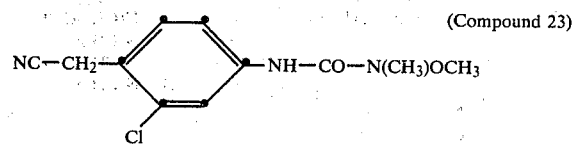

(a) 128 g of α-(3-chloro-4-nitrophenyl)-acetonitrile are introduced into a boiling mixture of 150 g of iron turnings, 4 ml of concentrated hydrochloric acid, 100 ml of water, 300 ml of alcohol and 150 ml of toluene. The mixture is refluxed for 4 hours and is then allowed to cool. There is subsequently added 1 liter of 0.5 N sodium hydroxide solution and the mixture is filtered. The filter residue is washed with toluene, the toluene solutions are separated and concentrated by evaporation, and the residue is distilled to thus obtain 57 g of α-(4-amino-3-chlorophenyl-)acetonitrile, m.p. 77°.

(b) 57 g of α-(4-amino-3-chlorophenyl)-acetonitrile are dissolved in 100 ml of ethyl acetate, and the solution is added dropwise at −20° to a solution of 40 g of phosgene in 300 ml of toluene. This solution is then stirred for 8 hours at room temperature, and is finally refluxed for one hour, after which the solvent is distilled off. The residue, consisting of oily α-(4-isocyanato-3-chlorophenyl)-acetonitrile, is added dropwise with stirring to a solution of 13.5 g of methoxymethylamine in 200 ml of acetonitrile. Ice-water is finally added to the reaction solution, as a result of which the urea precipitates. The resulting α-[4-(3-methoxy-3-methylureido)-3-chlorophenyl]-acetonitrile is collected by filtration and then recrystallised from diluted ethanol: yield 38 g; m.p. 104°.

The following compounds are produced in a manner analogous to that of the above Examples:

TABLE 1

| No. | Y | X | Z | NR₂R₃ | Phys. Data |
|-----|---|---|---|-------|------------|
| 1 | NC—CH₂— | H | H | N(CH₃)OCH₃ | m.p. 85–86° |
| 2 | NC—CH(CH₃)— | H | H | N(CH₃)OCH₃ | m.p. 103–104° |
| 3 | NC—C(CH₃)₂— | H | H | N(CH₃)OCH₃ | m.p. 94–95° |
| 4 | Cl—⟨⟩—CH(CN)— | | H | H | N(CH₃)OCH₃ | m.p. 96–97° |
| 5 | ⟨⟩—C(CH₃)(CN)— | H | H | NHCH₃ | m.p. 168–169° |
| 6 | ⟨⟩—C(CH₃)(CN)— | H | H | N(CH₃)OCH₃ | $n_D^{40}$ 1.5723 |
| 7 | NC—CH(C₂H₅)— | H | H | N(CH₃)₂ | m.p. 162–164° |
| 8 | NC—CH(C₂H₅)— | H | H | N(CH₃)OCH₃ | m.p. 67–68° |
| 9 | NC—C₂H₄— | H | H | N(CH₃)₂ | m.p. 91–93° |
| 10 | NC—C₂H₄— | H | H | N(CH₃)OCH₃ | m.p. 63–65° |

TABLE 1-continued $$\text{Y} - \underset{\text{Z}}{\overset{\text{X}}{\boxed{\phantom{X}}}} - \text{NH} - \text{CO} - \text{N} \overset{R_2}{\underset{R_3}{\phantom{N}}}$$

| No. | Y | X | Z | NR₂R₃ | Phys. Data |
|---|---|---|---|---|---|
| 11 | NC—CH(C₄H₉ sek)— | H | H | N(CH₃)OCH₃ | viscous oil |
| 12 | NC—C₂H₄— | 3-Cl | H | N(CH₃)₂ | m.p. 128° |
| 13 | NC—C₂H₄— | 3-Cl | H | N(CH₃)OCH₃ | m.p. 88–90° |
| 14 | NC—CH(CH₃)—CH₂— | H | H | N(CH₃)₂ | m.p. 103–104° |
| 15 | NC—CH(CH₃)—CH₂— | H | H | N(CH₃)OCH₃ | m.p. 99–101° |
| 16 | NC—C₂H₄— | 3-CF₃ | H | N(CH₃)₂ | m.p. 158–160° |
| 17 | NC—C₂H₄— | 3-CF₃ | H | N(CH₃)OCH₃ | m.p. 121–123° |
| 18 | cyclopropyl-CN | H | H | N(CH₃)₂ | m.p. 128–130° |
| 19 | cyclopropyl-CN | H | H | N(CH₃)OCH₃ | m.p. 104–105° |
| 20 | NC—CH(CH₃)— | 3-Cl | H | N(CH₃)₂ | |
| 21 | NC—CH(CH₃)— | 3-Cl | H | N(CH₃)OCH₃ | |
| 22 | NC—CH₂— | 3-Cl | H | N(CH₃)₂ | m.p. 176–178° |
| 23 | NC—CH₂— | 3-Cl | H | N(CH₃)OCH₃ | m.p. 104° |
| 24 | furyl-CH₂-CH(CN)- | H | H | N(CH₃)₂ | m.p. 155° |
| 25 | furyl-CH₂-CH(CN)- | H | H | N(CH₃)OCH₃ | m.p. 130° |
| 26 | furyl-CH₂CH(CN)- | 3-Cl | H | N(CH₃)₂ | |
| 27 | furyl-CH₂-CH(CN)- | 3-Cl | H | N(CH₃)OCH₃ | |
| 28 | NC—CH₂— | 3-CF₃ | H | NHC₂H₅ | m.p. 112° |
| 29 | NC—C₂H₄— | 3-CH₃ | H | N(CH₃)₂ | m.p. 96–97° |
| 30 | NC—C₂H₄— | 3-CH₃ | H | N(CH₃)OCH₃ | m.p. 30° |
| 31 | NC—CHCl—CH₂— | 3-Cl | H | N(CH₃)₂ | |
| 32 | NC—CHCl—CH₂— | 3-Cl | H | N(CH₃)OCH₃ | |
| 33 | NC—CHCl—CH₂— | H | H | NHCH₃ | |
| 34 | NC—CH(CH₃)—CH₂— | 3-CH₃ | H | N(CH₃)₂ | m.p. 83–85° |
| 35 | NC—CH(CH₃)—CH₂— | 3-CH₃ | H | N(CH₃)OCH₃ | |
| 36 | NC—CH(CH₃)—CH₂— | H | H | NHCH₃ | |
| 37 | NC—CH(C₆H₅)—CH₂— | H | H | N(CH₃)₂ | m.p. 134–138° |
| 38 | NC—CH₂— | 3-Cl | H | NHCH₃ | m.p. 162–164° |
| 39 | NC—CH₂— | 3-CF₃ | H | N(CH₃)₂ | m.p. 155° |
| 40 | NC—CH₂— | 3-CF₃ | H | N(CH₃)OCH₃ | m.p. 86° |
| 41 | NC—C₂H₄— | 3-Cl | H | N(CH₃)C₂H₅ | m.p. 93–95° |
| 42 | NC—(CH₂)₃— | H | H | N(CH₃)₂ | m.p. 79–82° |
| 43 | NC—(CH₂)₃— | H | H | N(CH₃)OCH₃ | m.p. 72° |
| 44 | NC—CH(CH₃)—CH(CH₃)— | H | H | N(CH₃)₂ | oil |
| 45 | NC—CH(CH₃)—CH(CH₃)— | H | H | N(CH₃)OCH₃ | oil |
| 46 | NC—CH₂—CH(CH₃)— | H | H | N(CH₃)OCH₃ | m.p. 30° |
| 47 | NC—CH₂—CH(CH₃)— | H | H | N(CH₃)₂ | m.p. 89–90° |
| 48 | NC—CH₂—CH(C₂H₅)— | H | H | N(CH₃)₂ | $n_D^{27} = 1.5658$ |
| 49 | NC—CH₂—CH(C₂H₅)— | H | H | N(CH₃)OCH₃ | $n_D^{25} = 1,5526$ |
| 50 | NC—CH(CH₃)—CH₂— | H | H | N(CH₃)₂ | m.p. 173° |
| 51 | NC—CH₂— | 3-CF₃ | H | N(CH₃)—n-C₄H₉ | m.p. 50° |
| 52 | NC—CH₂— | 3-CF₃ | H | N-morpholinyl-CH₃ | m.p. 157° |
| 53 | NC—CH₂— | 3-CF₃ | H | NHCH₃ | m.p. 126° |
| 54 | NC—CH₂— | 3-CF₃ | H | NH—n-C₄H₉ | m.p. 128–130° |
| 55 | NC—CH₂— | 3-Cl | H | N(CH₂—CH=CH₂)₂ | m.p. 87° |
| 56 | NC—CH₂— | 3-Cl | H | NH—CH₂—CH=CH₂ | m.p. 103–105° |
| 57 | NC—CH₂— | 3-Cl | H | morpholinyl | m.p. 136° |
| 58 | NC—CH₂— | 3-Cl | H | N-morpholinyl-CH₃ | m.p. 117–120° |
| 59 | NC—CH₂— | 3-Cl | H | N(CH₃)—n-C₄H₉ | m.p. 96–99° |

TABLE 1-continued $$\begin{array}{c} X \\ Y-\!\!\!\bigcirc\!\!\!-NH-CO-N\diagup_{R_3}^{R_2} \\ Z \end{array}$$

| No. | Y | X | Z | NR₂R₃ | Phys. Data |
|---|---|---|---|---|---|
| 60 | NC—CH₂— | 3-Cl | H | N(CH₃)—CH—CH₃<br>            |<br>            C≡CH | m.p. 99° |

TABLE 2

$$\begin{array}{c} X \diagdown \diagup Z \\ \bigcirc -NH-CO-N\diagup_{R_3}^{R_2} \\ Y \end{array}$$

| No. | Y | X | Z | NR₂R₃ | Phys. Data |
|---|---|---|---|---|---|
| 101 | NC—C₂H₄— | H | H | N(CH₃)₂ | m.p. 159–161° |
| 102 | NC—C₂H₄— | H | H | N(CH₃)OCH₃ | m.p. 72–72° |
| 103 | NC—C₂H₄— | 4-Br | H | N(CH₃)₂ | m.p. 147–149° |
| 104 | NC—C₂H₄— | 4-Br | H | N(CH₃)OCH₃ | m.p. 98–99° |
| 105 | NC—C₂H₄— | 4-Cl | H | N(CH₃)OCH₃ | m.p. 103–105° |
| 106 | NC—CH(CH₃)—CH₂— | 4-CH₃ | H | N(CH₃)₂ | |
| 107 | NC—CH(CH₃)—CH₂— | 4-CH₃ | H | N(CH₃)OCH₃ | |
| 108 | NC—C₂H₄— | 4-OCH₃ | H | N(CH₃)₂ | |
| 109 | NC—C₂H₄— | 4-OCH₃ | H | N(CH₃)OCH₃ | |
| 110 | NC—CH(CH₃)—CH₂— | 4-Cl | H | N(CH₃)₂ | m.p. 187–189° |
| 111 | NC—CH(CH₃)—CH₂— | 4-Cl | H | N(CH₃)OCH₃ | m.p. 82–84° |
| 112 | NC—C₂H₄— | H | H | N(CH₃)₂ | |
| 113 | NC—C₂H₄— | H | H | N(CH₃)OCH₃ | |
| 114 | NC—C₂H₄— | 2-Cl | 4-Cl | N(CH₃)OCH₃ | m.p. 80° |
| 115 | NC—C₂H₄— | 4-CH₂ | H | N(CH₃)₂ | m.p. 178–179° |
| 116 | NC—C₂H₄— | 4-CH₃ | H | N(CH₂)OCH₃ | m.p. 87–90° |
| 117 | NC—C₂H₄— | 4-CH₃ | H | NHCH₃ | m.p. 162–164° |
| 118 | NC—C₂H₄— | 4-Cl | H | N(CH₃)₂ | m.p. 163–164° |
| 119 | NC—CH(C₆H₅)—CH₂— | H | H | N(CH₃)₂ | m.p. 144–146° |
| 120 | NC—CH₂— | H | H | N(CH₃)OCH₃ | $n_D^{25} = 1.5513$ |
| 121 | NC—CH₂— | H | H | N(CH₃)₂ | m.p. 115° |

FORMULATION EXAMPLES

The processing of the compounds of the formula I into compositions usable in agriculture can be carried out for example according to the following instructions:

Example 3

Wettable powder

The following constituents are used to produce (a) a 70% wettable powder and (b) a 10% wettable powder:

(a)
- 70 parts of β-[m-(3,3-dimethylureido)-phenyl]-propionitrile (compound No. 101),
- 5 parts of sodium dibutyl-naphthalene sulfonate,
- 3 parts of naphthalenesulfonic acid/phenolsulfonic acid/formaldehyde condensate (3:2:1),
- 10 parts of kaolin, and
- 12 parts of Champagne chalk; and (b)
- 10 parts of α-[p-(3-methoxy-3-methylureido)-phenyl]-acetonitrile (compound No. 1),
- 3 parts of a mixture of the sodium salts of saturated fatty alcohol sulfates,
- 5 parts of naphthalenesulfonic acid/formaldehyde condensate, and
- 82 parts of kaolin.

The given active substance is absorbed onto the appropriate carriers (kaolin and chalk), and the material is subsequently mixed and ground with the remaining constituents. Wettable powders having excellent wetting and suspension properties are obtained. It is possible to obtain from wettable powders of this type, by dilution with water, suspensions containing 0.1 to 80% of active substance, these suspensions being suitable for combating weeds in crops of cultivated plants.

Example 4

Paste

The following materials are used to produce a 45% paste:
- 45 parts of α-[p-(3-methoxy-3-methylureido)-phenyl]-isobutyronitrile (compound No. 3),
- 5 parts of sodium aluminium silicate,
- 14 parts of cetyl polyglycol ether having 8 mols of ethylene oxide,
- 1 part of oleyl polyglycol ether having 5 mols of ethylene oxide,
- 2 parts of spindle oil,
- 10 parts of polyethylene glycol (mean molecular weight 400 g/mol)
- 23 parts of water.

The active substance is intimately mixed and ground with the additives in suitable apparatus. There is obtained a paste from which can be prepared suspensions of the desired concentration by dilution with water.

Example 5

Emulsion concentrate

The following constituents are mixed together to produce a 25% emulsion concentrate:
- 25 parts of β-[4-bromo-(3,3-dimethylureido)-phenyl]-propionitrile (compound No. 103), 10 parts of a mixture of nonylphenolpolyoxyethylene and calcium dodecylbenzene sulfonate,
10 parts of cyclohexanone, and
55 parts of xylene.

This concentrate can be diluted with water to give emulsions of suitable concentration, for example 0.1%, and these emulsions are suitable for combating weeds in crops of cultivated plants.

Example 6

Suspension concentrate

The following substances are used to produce a 45% suspension concentrate:

45 parts of α-[p-(3-methylureido)-phenyl]-α-phenyl-propionitrile (compound No. 5),
5 parts of ethylene glycol,
3 parts of octylphenoxypolyethylene glycol having 9–10 mols of ethylene oxide per mol of octylphenol),
3 parts of a mixture of aromatic sulfonesulfonic acids condensed with formaldehyde as ammonium salt,
1 part of silicone oil in the form of a 75% emulsion,
0.1 part of a mixture of 1-(3-chloroallyl)-3,5,7-triazonium-adamantane chloride with sodium carbonate, chloride value at least 11.5%,
0.2 part of a biopolymeric thickener having a maximum of 100 nuclei per gram, and
42.7 parts of water.

The active substance is intimately mixed and ground with the additives in apparatus suitable for the purpose. There is obtained a concentrate from which suspensions of any desired concentration can be prepared by dilution with water.

BIOLOGICAL EXAMPLES

The following test methods serve to demonstrate the suitability of the novel active substances of the formula I as herbicides (pre- and post-emergence).

Example 7

Pre-emergence herbicidal action

Immediately after sowing of the test plants in seed trays in a greenhouse, the surface of the soil is treated with an aqueous dispersion of the active substance, which has been prepared from a 25% emulsion concentrate, and from a 25% wettable powder containing active substances which cannot be produced as emulsion concentrates owing to inadequate solubility. A concentration of 4 kg of active substance per hectare is applied. The seed trays are kept in the greenhouse at 22°–25° with 50–70% relative humidity, and the test results are evaluated after three weeks, the results being assessed according to the following scale of ratings:

1 = plants have not germinated or have fully died off,
2–3 = very intense action,
4–6 = moderate action,
7–8 = slight action,
9 = no action (as in the case of untreated control plants).

| Pre-emergence action Applied amount: 4 kg of active substance/hectare | | | | |
|---|---|---|---|---|
| Compound No. | Avena | Setaria | Sinapis | Stellaria |
| 3 | 2 | 3 | 1 | 2 |
| 5 | 1 | 2 | 1 | 2 |
| 7 | 2 | 2 | 1 | 1 |

| -continued Pre-emergence action Applied amount: 4 kg of active substance/hectare | | | | |
|---|---|---|---|---|
| Compound No. | Avena | Setaria | Sinapis | Stellaria |
| 8 | 4 | 4 | 1 | 1 |
| 13 | 3 | 3 | 1 | 2 |
| 18 | 2 | 3 | 1 | 1 |
| 22 | 1 | 1 | 1 | 1 |
| 39 | 1 | 1 | 1 | 1 |
| 40 | 1 | 2 | 1 | 1 |
| 101 | 3 | 3 | 9 | 2 |
| 102 | 2 | 1 | 9 | 1 |

Example 8

Selective pre-emergence herbicidal action

A number of weed and cultivated plant seeds are tested using varying concentrations of active substance, corresponding to 4, 2, 1 and 0.5 kg/hectare, the test conditions being identical to those described in Example 7. The evaluation is made on the basis of the same scale of ratings.

| Action amount applied in kg of AS per hectare | Compound No. 23 | | | |
|---|---|---|---|---|
| test plant | 4 | 2 | 1 | 0.5 |
| barley | 9 | 9 | 9 | 9 |
| wheat | 7 | 9 | 9 | 9 |
| maize | 4 | 9 | 9 | 9 |
| Sorghum hybr. | 9 | 9 | 9 | 9 |
| upland rice | 2 | 4 | 7 | 9 |
| Avena fatua | 2 | 8 | 9 | 9 |
| Bromus téctorum | 2 | 3 | 3 | 9 |
| Lolium perenne | 5 | 8 | 9 | 9 |
| Alopecurus myos. | 2 | 5 | 7 | 9 |
| Digitaris sang. | 1 | 1 | 1 | 4 |
| Echinochloa s.g. | 2 | 8 | 9 | 9 |
| Sorghum halep. | 9 | 9 | 9 | 9 |
| Rottboellia ex. | 3 | 8 | 9 | 9 |
| Cyperus escul. | 5 | 9 | 9 | 9 |
| soya bean | 3 | 9 | 9 | 9 |
| cotton | 1 | 8 | 9 | 9 |
| Abutilon | 1 | 1 | 3 | 9 |
| Sida spinosa | 1 | 1 | 1 | 8 |
| Xanthium Sp. | 1 | 2 | 9 | 9 |
| Amaranthus ret. | 1 | 1 | 1 | 1 |
| Chenopodium Sp. | 1 | 1 | 1 | 1 |
| Solanum nigrum | 1 | 1 | 1 | 1 |
| Ipomoea | 2 | 7 | 9 | 9 |
| Sinapis | 1 | 1 | 1 | 4 |
| Stellaria | 1 | 1 | 1 | 2 |
| Chrysanthe. leuc. | 1 | 1 | 1 | 2 |
| Galium aparine | 1 | 3 | 8 | 9 |
| Viola tricolor | 1 | 1 | 2 | 4 |
| Veronica Sp. | 1 | 1 | 1 | 1 |

Also the other compounds of the formula I exhibited in this test an excellent herbicidal action against most dicotyledonous weeds and against some monocotyledonous weeds, the cultivated plants, such as wheat, barley, maize, millet, soya bean and cotton, not being damaged at all or being damaged only when higher amounts are applied.

Example 9

Pre-emergence herbicidal action in rape crops

Rapeseeds and some typical rape-weed seeds are tested and evaluated under the same conditions as in Example 7.

| Test plant | Pre-emergence action Compound No. 102 | | |
|---|---|---|---|
| | 4 kg/hect | 2 kg/hect | 1 kg/hect |
| rape "Gulle" | 9 | 9 | 9 |
| rape "Bistro" | 9 | 9 | 9 |
| Alopecurus myos. | 4 | 6 | 8 |
| Matricaria cham. | 1 | 1 | 1 |
| Papaver rhoeas | 1 | 1 | 2 |
| Rumex crispus | 3 | 4 | 6 |
| Stellaria media | 1 | 4 | 5 |

Compound No. 101 exhibits a similar sphere of activity.

Example 10

Post-emergence herbicidal action (contact herbicide)

A number of weeds, both monocotyledonous and dicotyledonous, are sprayed after emergence (in the 4- to 6-leaf stage) with an aqueous active-substance dispersion in a dosage of 4 kg of active substance per hectare, and the sprayed weeds are kept at 24°–26° with 45–60% relative humidity. The test is evaluated at least 15 days after the treatment, and the results are assessed according to the scale of ratings used in the pre-emergence test (Example 7).

| Comp. No. | Post-emergence action Applied amount: 4 kg of active substance/hectare | | | | | |
|---|---|---|---|---|---|---|
| | Avena | Setaria | Lolium | Solanum | Sinapis | Stellaria |
| 1 | 5 | 4 | 7 | 1 | 1 | 1 |
| 2 | 1 | 1 | 1 | 1 | 1 | 1 |
| 3 | 1 | 2 | 3 | 1 | 1 | 1 |
| 4 | 2 | 2 | 5 | 1 | 1 | 1 |
| 5 | 2 | 3 | 4 | 1 | 1 | 1 |
| 6 | 2 | 1 | 2 | 1 | 1 | 1 |
| 7 | 3 | 1 | 2 | 1 | 1 | 1 |
| 8 | 4 | 2 | 5 | 1 | 1 | 1 |
| 11 | 3 | 1 | 2 | 1 | 1 | 1 |
| 12 | 2 | 1 | 3 | 1 | 1 | 1 |
| 14 | 4 | 2 | 5 | 1 | 1 | 1 |
| 15 | 5 | 4 | 5 | 1 | 1 | 1 |
| 19 | 1 | 1 | 5 | 1 | 1 | 1 |
| 22 | 2 | 2 | 2 | 1 | 1 | 1 |
| 23 | 1 | 1 | 3 | 1 | 1 | 1 |
| 29 | 3 | 1 | 6 | 1 | 1 | 1 |
| 34 | 1 | 3 | 3 | 1 | 1 | 1 |
| 38 | 5 | 5 | 6 | 1 | 1 | 1 |
| 39 | 2 | 2 | 2 | 1 | 1 | 1 |
| 40 | 2 | 1 | 2 | 1 | 1 | 1 |
| 41 | 6 | 5 | 6 | 1 | 1 | 1 |
| 42 | 4 | 6 | 4 | 1 | 1 | 1 |
| 44 | 4 | 4 | 3 | 1 | 1 | 1 |
| 45 | 6 | 4 | 5 | 1 | 1 | 2 |
| 46 | 5 | 5 | 4 | 1 | 1 | 1 |
| 47 | 4 | 4 | 4 | 1 | 1 | 1 |
| 48 | 4 | 4 | 4 | 1 | 1 | 1 |
| 114 | 7 | 3 | 6 | 1 | 1 | 1 |
| 119 | 5 | 7 | 6 | 1 | 1 | 1 |
| 120 | 5 | 3 | 5 | 1 | 1 | 1 |

Example 11

Under the same test conditions as in Example 10, a number of weeds and cultivated plants are tested at various concentrations of active substances, corresponding to 4, 2, 1 and 0.5 kg per hectare and 2, 1, 0.5 and 0.25 kg per hectare, respectively. An evaluation is made on the basis of the same scale of ratings.

| Action amount applied kg of AS/hect. test plant | Compound No. 23 | | | | Compound No. 38 | | | | Compound No. 102 | | | |
|---|---|---|---|---|---|---|---|---|---|---|---|---|
| | 2 | 1 | 0.5 | 0.25 | 4 | 2 | 1 | 0.5 | 4 | 2 | 1 | 0.5 |
| barley | 3 | 8 | 9 | 9 | 9 | 9 | 9 | 9 | 4 | 7 | 9 | 9 |
| wheat | 2 | 4 | 9 | 9 | 8 | 9 | 9 | 9 | 4 | 7 | 7 | 8 |
| maize | 1 | 3 | 7 | 9 | 7 | 9 | 9 | 9 | 6 | 9 | 9 | 9 |
| Sorghum hybr. | 4 | 7 | 9 | 9 | 8 | 9 | 9 | 9 | 7 | 8 | 9 | 9 |
| upland rice | 2 | 3 | 7 | 9 | 7 | 7 | 9 | 9 | 2 | 4 | 7 | 9 |
| Avena fatua | 1 | 2 | 7 | 9 | 6 | 8 | 9 | 9 | 2 | 3 | 6 | 9 |
| Bromus tectorum | 1 | 2 | 2 | 7 | 6 | 9 | 9 | 9 | 7 | 7 | 8 | 9 |
| Lolium perenne | 3 | 3 | 9 | 9 | 9 | 9 | 9 | 9 | 4 | 6 | 9 | 9 |
| Alopecurus myos. | 2 | 2 | 8 | 9 | 3 | 6 | 9 | 9 | 2 | 3 | 3 | 8 |
| Digitaria sang. | 1 | 1 | 1 | 2 | 1 | 3 | 9 | 9 | 3 | 3 | 6 | 9 |
| Echinochloa c.g. | 1 | 1 | 2 | 7 | 7 | 9 | 9 | 9 | 7 | 9 | 9 | 9 |
| Sorghum halep. | 9 | 9 | 9 | 9 | 9 | 9 | 9 | 9 | 9 | 9 | 9 | 9 |
| Rottboellia ex. | 1 | 1 | 2 | 4 | 9 | 9 | 9 | 9 | 4 | 4 | 8 | 9 |
| Cyperus escul. | 4 | 4 | 7 | 9 | 4 | 6 | 9 | 9 | 7 | 7 | 9 | 9 |
| soya bean | 1 | 1 | 1 | 2 | 3 | 6 | 8 | 9 | 1 | 2 | 2 | 3 |
| cotton | 2 | 2 | 3 | 4 | 8 | 9 | 9 | 9 | 1 | 1 | 1 | 2 |
| Abutilon | 1 | 1 | 1 | 1 | 2 | 2 | 3 | 3 | 1 | 1 | 1 | 1 |
| Sida spinosa | 1 | 1 | 2 | 3 | 4 | 6 | 8 | 9 | 2 | 6 | 7 | 7 |
| Xanthium Sp. | 1 | 1 | 1 | 1 | 1 | 1 | 2 | 2 | — | — | — | — |
| Amaranthus ret. | 1 | 1 | 1 | 1 | 1 | 2 | 5 | 6 | 1 | 1 | 4 | 4 |
| Chenopodium Sp. | 1 | 1 | 1 | 1 | 1 | 1 | 1 | 1 | — | — | — | — |
| Solanum nigrum | 1 | 1 | 1 | 1 | 1 | 1 | 1 | 1 | 1 | 1 | 1 | 1 |
| Ipomoea | 1 | 1 | 1 | 1 | 1 | 1 | 2 | 9 | 1 | 1 | 2 | 3 |
| Sinapis | 1 | 1 | 1 | 1 | 1 | 1 | 1 | 1 | 9 | 9 | 9 | 9 |
| Stellaria | 1 | 1 | 1 | 1 | 1 | 1 | 1 | 2 | 1 | 1 | 2 | 2 |
| Chrysanthe. leuc. | 1 | 1 | 1 | 1 | 1 | 1 | 1 | 1 | 1 | 1 | 3 | 4 |
| Galium aparine | 1 | 1 | 1 | 2 | 1 | 1 | 1 | 6 | 2 | 2 | 3 | 7 |
| Viola tricolor | 1 | 2 | 4 | 5 | 1 | 2 | 3 | 7 | — | — | — | — |
| Veronica Sp. | 1 | 1 | 1 | 1 | 1 | 1 | 6 | 7 | — | — | — | — |
| Portulaca | | | | | — | — | — | — | 1 | 1 | 1 | 1 |
| Kochia scop. | | | | | — | — | — | — | 1 | 1 | 1 | 2 |

-continued

| Action amount applied kg of AS/hect. | Compound No. 23 | | | | Compound No. 38 | | | | Compound No. 102 | | | |
|---|---|---|---|---|---|---|---|---|---|---|---|---|
| test plant | 2 | 1 | 0.5 | 0.25 | 4 | 2 | 1 | 0.5 | 4 | 2 | 1 | 0.5 |
| Sesbania | — | — | — | — | — | — | — | — | 1 | 1 | 1 | 1 |

The compounds of the formula I exhibited also in this test excellent activity against most dicotyledonous weeds and against some monocotyledonous weeds, the cultivated plants: soya bean, maize, varieties of cereals, barley, millet, wheat and cotton suffering no damage or suffering damage only when higher amounts were applied.

In addition to having a good contact-herbicidal action, some compounds of the formula I, particularly the compounds Nos. 101 and 102, exhibited surprisingly good selectivity in rape crops.

What is claimed is:

1. A cyanoalkyl-phenylurea of the formula I

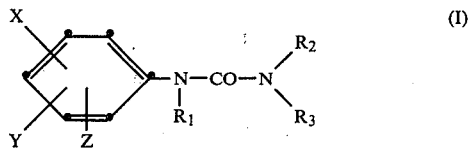

(I)

wherein
X is hydrogen, halogen, trifluoromethyl, methyl or methoxy,
Y is a cyanoalkyl group 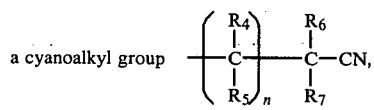

Z is hydrogen or halogen,
n is the number 0, 1 or 2,
$R_1$ is hydrogen or $C_1$–$C_6$-alkyl,
$R_2$ is hydrogen, $C_1$–$C_6$-alkyl, $C_1$–$C_6$-alkoxy, $C_2$–$C_6$-alkenyl or $C_3$–$C_6$-alkynyl,
$R_3$ is hydrogen, $C_1$–$C_6$-alkyl or $C_2$–$C_6$-alkenyl, or
$R_2$ and $R_3$ together with the nitrogen atom to which they are bound form a 5–7-membered heterocycle, which can contain as ring member also an oxygen or sulfur atom or an imino group,
$R_4$, $R_5$ and $R_6$ are each hydrogen, $C_1$–$C_6$-alkyl and $C_1$–$C_6$-haloalkyl,
$R_7$ is hydrogen, $C_1$–$C_6$-alkyl, aralkyl, particularly benzyl, phenyl or $C_1$–$C_6$-alkoxy, or
$R_6$ and $R_7$ together with the carbon atom carrying them can form a $C_3$–$C_7$-cycloalkyl ring.

2. A compound of the formula I according to claim 1, wherein the cyanoalkyl substituent Y occupies the para- or meta-position of the phenyl ring.

3. A compound of the formula I according to claim 1, wherein n is zero or one.

4. A compound of the formula I according to claim 1, wherein $R_2$ is hydrogen, methyl or methoxy, and $R_3$ is methyl.

5. A compound of the formula I according to claim 1, wherein $R_1$ is hydrogen.

6. A compound of the formula I according to claim 1, wherein Z is hydrogen.

7. A compound of the formula I according to claim 1, wherein X is hydrogen, halogen or trifluoromethyl.

8. A compound of the formula I according to claim 1, wherein the cyanoalkyl substituent Y occupied the para-position of the phenyl ring, and n is zero.

9. A compound of the formula I according to claim 1, wherein the cyanoalkyl substituent Y occupies the meta-position of the phenyl ring, and n is one.

10. A compound of the formula I according to claim 1, wherein the substituent Y is in the para-position and the substituent X in the meta-position of the phenyl ring, n is zero, $R_1$ and Z are each hydrogen, $R_2$ is hydrogen, methyl or methoxy, $R_3$ is methyl, and X is hydrogen, chlorine or trifluoromethyl.

11. A compound of the formula I according to claim 1, wherein the substituent Y is in the meta-position of the phenyl ring, n is one, $R_1$, X and Z are each hydrogen, $R_2$ is hydrogen, methyl or methoxy, and $R_3$ is methyl.

12. A compound according to claim 1 which is β-[4-(3,3-dimethylureido)-3-chlorophenyl]-propionitrile.

13. A compound according to claim 1 which is β-[4-(3-methoxy-3-methylureido)-3-chlorophenyl]-propionitrile.

14. A compound according to claim 1 which is β-[3-(3-methoxy-3-methylureido)-phenyl]-propionitrile.

15. A compound according to claim 1 which is β-[3-(3,3-dimethylureido)-phenyl]-propionitrile.

16. A compound according to claim 1 which is α-[4-(3-methoxy-3-methylureido)-3-chlorophenyl]-acetonitrile.

17. A compound according to claim 1 which is α-[4-(3,3-dimethylureido)-3-chlorophenyl]-acetonitrile.

18. A compound according to claim 1 which is α-[4-(3,3-dimethylureido)-3-trifluoromethylphenyl]-acetonitrile.

19. A compound according to claim 1 which is β-[4-(3,3-dimethylureido)-3-methylphenyl]-α-methylpropionitrile.

20. A herbicidal composition comprising a herbicidally effective amount of at least one compound according to claim 1, together with a suitable carrier therefor.

21. A method for selectively combating weeds in crops of cultivated plants, which method comprises applying thereto or to the locus thereof a herbicidally effective amount of a compound according to claim 1.

22. A method according to claim 21, wherein the crop is rape.

23. A method according to claim 21, wherein the crop is wheat, barley, maize or millet.

* * * * *